(12) United States Patent
Hacker et al.

(10) Patent No.: US 8,388,135 B2
(45) Date of Patent: Mar. 5, 2013

(54) OPHTHALMOLOGIC BIOMETRIC OR IMAGE GENERATING SYSTEM AND METHOD FOR DETECTION AND EVALUATION OF MEASURED DATA

(75) Inventors: Martin Hacker, Jena (DE); Thomas Pabst, Stadtroda (DE); Ralf Ebersbach, Schmölln (DE); Gerard Antkowiak, Jena (DE); Wilfried Bissmann, Jena (DE); Matthias Reich, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 193 days.

(21) Appl. No.: 12/886,155

(22) Filed: Sep. 20, 2010

(65) Prior Publication Data

US 2011/0069279 A1    Mar. 24, 2011

(30) Foreign Application Priority Data

Sep. 18, 2009 (DE) .......... 10 2009 041 996

(51) Int. Cl.
*A61B 3/10* (2006.01)
*A61B 3/14* (2006.01)
*A61B 3/00* (2006.01)
(52) U.S. Cl. ......... 351/221; 351/209; 351/246; 351/206
(58) Field of Classification Search ........... 351/200–246
See application file for complete search history.

(56) References Cited

U.S. PATENT DOCUMENTS

| 4,631,580 | A | * | 12/1986 | Taube et al. ............... 348/47 |
| 5,235,180 | A | | 8/1993 | Montagu |
| 5,321,501 | A | | 6/1994 | Swanson et al. |
| 5,847,827 | A | | 12/1998 | Fercher |
| 6,325,512 | B1 | | 12/2001 | Wei |
| 6,404,531 | B1 | | 6/2002 | Diedrich et al. |
| 6,443,449 | B1 | | 9/2002 | Takagi et al. |

(Continued)

FOREIGN PATENT DOCUMENTS

| DE | 198 57 001 A1 | 6/2000 |
| DE | 10 2007 046 507 A1 | 4/2009 |

(Continued)

OTHER PUBLICATIONS

Han, Shuo, et al., "Handheld forward-imaging needle endoscope for ophthalmic optical coherence tomography inspection," *Journal of Biomedical Optics*, vol. 13(2), Mar./Apr. 2008, pp. 020505-1-020505-3.

*Primary Examiner* — Mohammed Hasan
(74) *Attorney, Agent, or Firm* — Patterson Thuente Pedersen, P.A.

(57) ABSTRACT

An ophthalmological biometric or image-producing system and method for detection and analysis of measurement data including a measurement arrangement with an illumination unit for illuminating the eye with at least one measurement beam, a signal detection unit for the detection of the light portions scattered or reflected back from the eye, a central control unit with an output unit, and a pattern generating unit which includes an optical scan unit, a control unit as well as a position sensor for measuring the realized deflections of the optical scan unit, whereby control unit, optical scan unit and position sensor can form a control circuit. Thereby, the position sensor, except for the connection within the possible control circuit, includes a connection to a unit of the measurement arrangement for optimizing measurement value logging or to the central control unit for correcting the biometric measurements or tomograms.

28 Claims, 5 Drawing Sheets

U.S. PATENT DOCUMENTS

| | | |
|---|---|---|
| 6,654,127 B2 | 11/2003 | Everett et al. |
| 6,726,325 B2 | 4/2004 | Xie et al. |
| 6,769,769 B2 | 8/2004 | Podoleanu et al. |
| 6,810,140 B2 | 10/2004 | Yang et al. |
| 6,956,491 B2 | 10/2005 | Bown |
| 7,232,229 B2 | 6/2007 | Peeters et al. |
| 7,284,859 B2 | 10/2007 | Ferguson |
| 7,365,856 B2 | 4/2008 | Everett et al. |
| 7,374,287 B2 | 5/2008 | Van de Velde |
| 7,400,410 B2 | 7/2008 | Baker et al. |
| 7,414,779 B2 | 8/2008 | Huber et al. |
| 2003/0179366 A1* | 9/2003 | Takahashi ............... 356/139.1 |
| 2004/0061865 A1 | 4/2004 | Drabarek |
| 2006/0228011 A1 | 10/2006 | Everett et al. |
| 2007/0291277 A1 | 12/2007 | Everett et al. |
| 2008/0186501 A1 | 8/2008 | Xie |
| 2008/0285043 A1 | 11/2008 | Fercher et al. |
| 2010/0284021 A1 | 11/2010 | Hacker |

FOREIGN PATENT DOCUMENTS

| | | |
|---|---|---|
| EP | 1 872 713 A1 | 1/2008 |
| EP | 2 022 391 A1 | 2/2009 |
| EP | 1 775 545 B1 | 5/2009 |
| EP | 2 147 634 A1 | 1/2010 |
| JP | 2008-188047 | 8/2008 |
| WO | WO 02/40936 A1 | 5/2002 |
| WO | WO 2006/077107 A1 | 7/2006 |
| WO | WO 2008/151821 A1 | 12/2008 |

* cited by examiner

OPHTHALMOLOGIC BIOMETRIC OR IMAGE GENERATING SYSTEM AND METHOD FOR DETECTION AND EVALUATION OF MEASURED DATA

This application claims priority to German Patent Application No. 10 2009 041 996.9 filed on Sep. 18, 2009, said application is incorporated herein by reference in it's entirety.

FIELD OF THE INVENTION

The invention relates to an ophthalmological biometric or image-producing system and method for detection and analysis of measurement data, for determining sizes, distances and/or geometric relations of eye structures.

BACKGROUND

These measurements are necessary, for example, for the adjustment of implants, such as intraocular lenses after cataract surgery.

However, due to the increasing complexity and desired individualization of the implants, measurement data of more than one depth profile (A-scan) of the eye, particularly of several laterally offset A-scans, are required.

Other ophthalmological devices serve primarily for producing and evaluating two-dimensional images, sectional images, and volume scans of various areas of the eye with regard to the visual impression, sizes and distances of certain eye structures. Solutions thereto are known from prior art which apply optical scan systems.

A first group thereto are tomography systems, which, e.g., are based on the so-called OCT (optical coherence tomography) method, whereby coherent light is employed on reflective and scattering samples with the help of a interferometer for distance measurements and imaging. Through depth scans, the optical coherence tomography on the human eye delivers measurable signal responses due to the changes in the index of refraction at optical boundaries and due to volume scattering.

For example, the basic principle of the OCT method described in U.S. Pat. No. 5,321,501 is based on white-light interferometry and compares the duration of a signal by means of an interferometer (most often a Michelson interferometer). Thereby, the arm with known optical path length (=reference arm) is used as reference to the measurement arm, in which the sample is located. The interference of the signals from both arms results in a pattern with which the scattering amplitude, in dependence of the optical delays between the arms, can be determined, resulting in a depth-dependent scattering profile which, analogous to ultrasound technology, is called an A-scan. Quick variations of the optical delays between measurement and reference arm can be realized, e.g., by means of fiber links (EP 1 337 803 A1) or so-called rapid-scanning optical delays (RSOD) (U.S. Pat. No. 6,654,127 B2). In the multidimensional raster scan method, the beam is then transversally guided in one or two directions, allowing for a two-dimensional B-scan or a three-dimensional volume tomogram to be recorded. If the length of the reference arm is kept constant, a two-dimensional C-scan can be recorded through lateral scanning of the measurement beam in two directions.

The solution described in US 2007/0291277 A1 also refers to a device based on the OCT method. Contrary to the previously described solution, a Mach-Zehnder interferometer with a fiber reference path is used herein. Imaging of the optical coherence scanning device is said to be improved through different auxiliary equipment and/or functions, such as a fundus imaging device, an iris viewer, a motorized chin rest, and internal control of the instrument alignment.

A second group consists of confocal scanner-based ophthalmoscopes, particularly confocal scanning laser ophthalmoscopes (cSLO) which, in addition to the OCT-based tomography systems, also represent known and important tools for diagnosis and therapy in ophthalmology (U.S. Pat. No. 6,769,769 B2).

Confocal scanners can achieve a three-dimensional spatial resolution through limiting the depth of a spatially-adjustable focus by means of spatial filtering and, compared to OCT, do not rely on the utilization of interference effects.

Solutions for laser scanning ophthalmoscopes are described, for example, in U.S. Pat. No. 7,284,859 A and U.S. Pat. No. 7,374,287 B2.

Aside from fluorescence or indocyanine green angiography, laser scanning ophthalmoscopes can also be used for detecting different retinal diseases from the recorded fundus autofluorescence images (FAF images). Through excitation with light of a suitable wavelength and the appropriate filters, different retinal diseases become detectable. Changes of the topographic FAF intensity distribution appear with various retinal pathologies, such as age-related macular degeneration (AMD), macular edema, and genetically determined retinopathies. As with OTC, a glaucoma diagnosis is possible through the measuring of form and size of the optic nerve head. With this method, scattering profiles are also obtained from the response signal. Since the backscatter at the optical boundaries is particularly high due to the refractive indices, the determination of the optical path lengths between the boundaries is therefore also possible (WO 2008/151821A1).

In order to obtain the images in the form of two-dimensional images, sectional images, and volume scans required for the diagnosis, scans, in addition to A-scans (individual depth profiles), are required transversally in a first (B-scans) and a second direction (volume scans). Thereby it is very important to record those scans very quickly since the available attention span of a patient (with barely 2 sec.) is very limited.

Therefore, very quick deflection systems for the measurement beams must be deployed in such imaging systems.

At the same time, said deflection systems must be able to render a predetermined scan pattern very accurately, linearly, and very reproducibly, ensuring that the emerging sectional images and volume scans exhibit no distortions which would make the evaluation of the structures needlessly difficult. This is a contradiction with conventional galvanometer scanners since the resonant variations may be able to scan very quickly but are very often limited to sine-like scan patterns. However, other patterns can only be realized with slower and more elaborate non-resonant galvanometer scanners.

Said great challenges to the deflection equipment regarding speed, control accuracy, and linearity are, e.g., further enhanced when so-called tracking systems, already widely used in ophthalmology, are used which detect, register and/or actively compensate the eye movements during the course of the measurements. Such tracking systems are described, for example, in U.S. Pat. No. 6,726,325 B2; US 2006/228011 A1; U.S. Pat. No. 6,325,512 B1; and U.S. Pat. No. 7,365,856 B2.

Alternatively to active tracking, tomogram distortions due to interfering eye movements can be corrected through appropriate referencing with quick, more stable OCT scans in certain directions (WO 2006/077107 A1).

In order to meet these requirements, stably rotating polygon mirrors for realizing close to linear sawtooth or triangular scans, or galvanometer mirrors within closed control loops are used, according to prior art. Polygon mirrors are able to scan very quickly and stably but are limited to a defined deflection pattern in a defined direction. Additionally, they are very loud and expensive.

By contrast, galvanometer mirrors are able to realize different scan patterns but also require great electronic control efforts (U.S. Pat. No. 6,956,491 B2 and U.S. Pat. No. 6,433,449 B1) in order to reproduce a predetermined deflection pattern with accuracy, linearity, and reproducibility acceptable for imaging.

Therefore, elaborate combinations of both deflection systems are also employed as optical scan unit in ophthalmological devices, whereby a quickly rotating polygon mirror produces a fixed deflection pattern in a deflection direction and a galvanometer mirror realizes a deviating and, within certain limits, flexible deflection pattern in a second, slower deflection direction (U.S. Pat. No. 7,374,287 B2 and U.S. Pat. No. 6,810,140 B2).

Further known optical scan units are positionally adjustable, diffractive or refractive optical elements, such as rotating prisms (S. Han et al., Journal of Biomedical Optics, Vol. 13, 020505-1 (2008), or electrostatically deflected miniature mirrors (MEMS, US 2008/0186501 A1), acousto-optical (AOM) and electro-optical modulators (EOM; U.S. Pat. No. 6,404,531 B1). In principle, deformable mirrors and liquid crystal modulators for beam deflection are also suitable but in general slow by comparison.

The solutions for deflection systems for scanning measurement value logging, which are known in accordance with prior art and described herein, have the disadvantage of being very elaborate and expensive.

The example of a system for measurement beam deflection for an OCT system, according to prior art (US 2007/0291277 A1) is described in FIGS. 1a and 1b. Thereby, the OCT system, shown in FIG. 1a as functional schematic, consists of an illumination unit, an interferometer, a signal detection, and a central control unit with output unit. For the realization of B- and C-scans as well as volume scans, the measurement arm of the interferometer contains a deflection and/or scan unit, which exhibits connections to the central control unit.

The central control unit activates a pattern generation for one or even both scan directions, which transmits the patterns to be realized to the additionally existing control of the optical scan unit. In order to ensure that the produced scan pattern corresponds as close as possible to the pattern to be mapped, the general arrangement also exhibits a control circuit or control loop with at least one position sensor, which supplies the feedback signal. While the control sets the pattern to be generated as nominal value, the actually mapped pattern is determined by the position sensor. In the control circuit, the differences between nominal and actual values are determined and utilized by the control unit of the optical scan unit for minimizing the amount [nominal—actual].

Thereto, FIG. 1b shows in a diagram a predetermined nominal pattern (dotted line) as well as an effectively mapped actual pattern (solid line). Due to the limited capabilities of the scan unit, the deviations are caused by a predetermined, particularly quickly changing pattern and can be minimized with great effort but never entirely avoided. Depending on the settings of the control circuit or control loop, an incomplete following ("creeping approximation") of the actual pattern with regard to the intended pattern or, contrarily, overcompensation can occur ("overshoot" as shown in FIG. 1b). The properties of an optical scan unit including control circuit can be described through a transfer function between nominal and actual patterns, which can be measured and their properties taken into consideration for the pattern generation.

In the central control unit, respective signals are reconstructed from the acquired measurement values and images generated and, if applicable, biometric data calculated.

SUMMARY OF THE INVENTION

The invention herein is based on the task of realizing a system for deflection of measurement beams for ophthalmological biometric or image-producing systems, whereby the known disadvantages from prior art are remedied and which is significantly more cost-effective and less elaborate.

Furthermore, it should allow for the recording of undistorted tomograms and accurate biometric data.

According to an embodiment of the invention, the task, through the ophthalmological biometric or image-producing system, based on a measurement arrangement with an illumination unit for illuminating the eye with at least one measurement beam, a signal detection unit for capturing the light portions scattered or reflected back from the eye, a central control unit with output unit and a central control unit-activated pattern generating unit which exhibits an optical scan unit, a control unit for controlling the deflection of at least one measurement beam with regard to the eye structures, as well as a position sensor for measuring the realized deflections of the optical scan unit, whereby control unit, optical scan unit, and position sensor can form a control circuit or control loop, is solved in such a way that the position sensor, in addition to the connection within the possible control circuit or control loop, exhibits a connection to a unit of the measurement arrangement for optimizing measurement value logging or to the central control unit for correcting the biometric measurements or tomograms.

The term "biometry" herein encompasses but is not limited to the measurements as well as the measurement and analysis methods for the determination of distances within the eye.

By contrast, the term "image production" includes any and all mapping methods or imaging methods. While the object to be recorded is mapped directly as a two-dimensional image with the mapping method, two- or even three-dimensional images or a real object are produced from measurement parameters through the imaging method, whereby the measurement parameter, or information derived therefrom, is visualized through spatial resolution and encoded via colors or density value.

Thereby, particularly the generation of sectional images, also called tomograms, is included, which depict the inner spatial structure of an object. A sectional image or tomogram reproduces the inner structures in the way they would be available after cutting open or excising a thin slice from the object.

Even though the suggested optical scan unit is designed, particularly, for use in ophthalmological biometric or image-producing systems, which are based on an interferometric measurement arrangement, its application is not limited to said systems. The optical scan unit and the method for measurement value logging are, in principle, applicable in other ophthalmological measurement arrangements as well as measurement arrangements of unrelated technical areas.

BRIEF DESCRIPTION OF THE DRAWINGS

In the following, the invention will be further described by means of embodiment examples.

FIG. 1b is a position-time diagram depicting a nominal and an actual pattern for the OCT system in FIG. 1a;

FIG. 2b is a position-time diagram depicting a nominal and an actual pattern for the optical scan unit in FIG. 2a;

FIG. 2c is a juxtaposition of a distorted and a distortion-corrected tomogram, according to FIG. 2a;

FIG. 3c is a depiction of a position-time diagram of a triggered scan pattern, according to FIG. 3a.

DETAILED DESCRIPTION

Figure 1A:
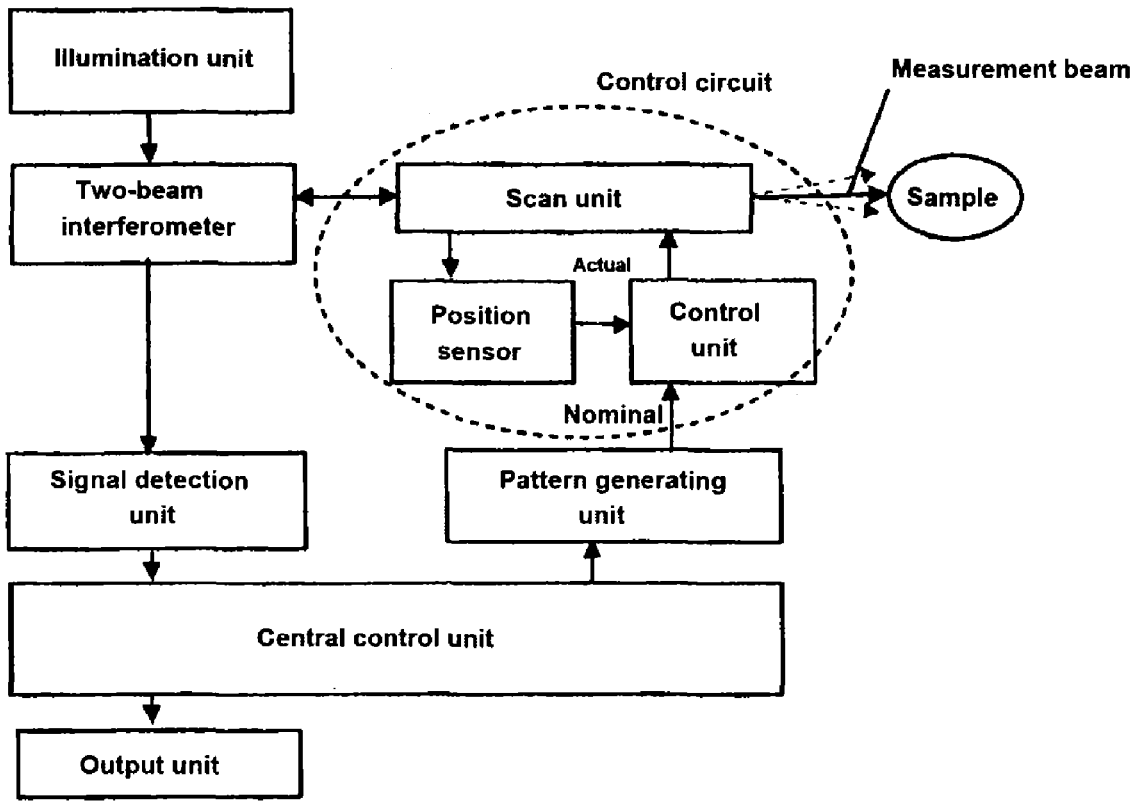
FIG. 1a is a functional schematic of an OCT system, according to known prior art.
Figure 1B:

A ophthalmological biometric or image-producing system, according to an example embodiment of the invention, is based on an interferometric measurement arrangement, which includes an illumination unit, a two-beam interferometer, such as a Michelson or Mach-Zehnder interferometer, a signal detection as well as a central control unit with output unit, and which includes a pattern generating unit for the optical scan unit, which is activated via the central control unit. The pattern generating unit includes an optical scan unit, a control unit for controlling the deflection of at least one measurement beam with regard to the eye structure as well as a position sensor for measuring the realized deflections of the optical scan unit, whereby the control unit, optical scan unit, and position sensor can form a control circuit or control loop.

Thereby, the pattern generating unit can, for example be a memory unit, which contains a value table, the values of which are read incrementally, transformed for example into analog voltage ratings and consecutively transmitted to the control unit. According to the invention, the position sensor, in addition to the connection within the possible control circuit, includes a connection to a unit of the measurement arrangement for the optimization of the measurement value logging or to the central control unit for correcting the biometric measurements or tomograms.

Hereby, the optical scan unit, which includes at least one galvanometer mirror, is positioned in the measurement arm of the two-beam interferometer and has a closed control circuit for the realization of the scan movements and damping of mechanical interferences. Thereto, the closed control circuit exhibits a scanner control unit for the realization of the scan patterns transmitted by the pattern generating unit, and at least one position sensor for detection of the actual positions of the galvanometer mirror during the realization of the scan pattern. For the purpose of transmitting said actual positions, the position sensor exhibits, for example connections to the central control unit, which utilizes the transmitted actual positions of the galvanometer mirror for corrections of the measured values.

The term "two-beam interferometer" is hereby not limited to the classic two-beam interferometers, such as Michelson or Mach-Zehnder interferometer. Similarly, variations of Michelson or Mach-Zehnder interferometers as measurement arrangement are contemplated, which exhibit several reference or measurement arms. With such measurement arrangements, according to US 2008/0285043 A1 and DE 10 2007 046 507 A1, for example, several measurement areas can be detected simultaneously.

In an example embodiment, the scan unit consists of only one mirror, which scans either one or two directions. For the detection of the actual positions of the galvanometer mirror, position sensors are used hereto. They can be realized either one- or two-dimensionally (position sensitive detector, U.S. Pat. No. 7,232,229 B2). Even though the position sensor can be based on different measurement principles, such as capacitive, inductive, potentiometric, magnetic (U.S. Pat. No. 5,177,631 A), magneto-strictive, or the like, optical position sensors are beneficial since the optical position detection is precise and, above all, not susceptible to interference due to triangulation or intensity modulation (U.S. Pat. No. 5,235,180 A).

The position signals for use in the control circuit are, preferably, analog signals, while they are, preferably, digitalized for transmission and storage in the central control unit by a digitization unit, which is not shown in the drawings for reasons of better clarity. If the position information is absolute, the resolution of the position signal should be greater than the one of the absolute pattern values. However, relative change of position values, which put fewer demands on resolutions and bit depths, can also be utilized.

Figure 2A:
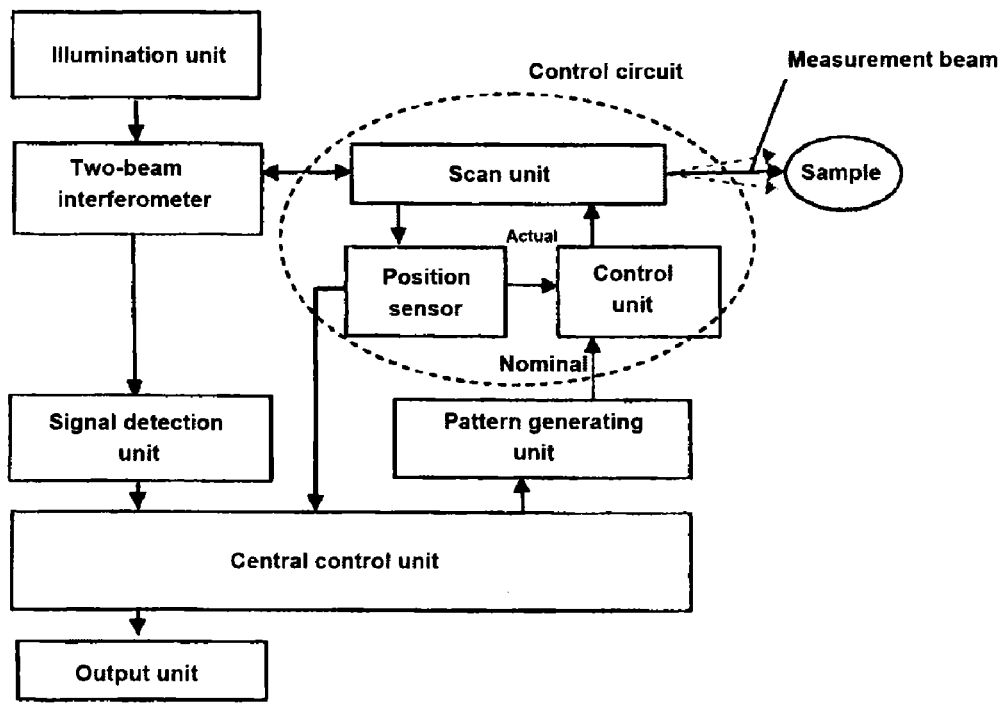
FIG. 2a is a functional schematic of an ophthalmological biometric system, according to an embodiment of the invention.

Thereto, FIG. 2a shows a functional schematic of a scan unit for ophthalmological biometric systems, including a illumination unit, a two-beam interferometer, a signal detection as well as a central control unit with output unit and pattern generator. The scan unit, which includes a galvanometer mirror, is positioned in the measurement arm of the two-beam interferometer and has a closed control circuit for realization of the scan movements and damping of interferences. Thereto, the closed control circuit includes a scanner control unit with an electronic regulating circuit for realization of the scan pattern, which is transmitted by the pattern generator, and at least one position sensor for detection of the actual positions of the galvanometer mirror during realization of the scan pattern.

For transmission of said actual positions, the position sensor includes connections to the central control unit. The transmitted actual positions of the galvanometer mirror are utilized by the central control unit for correcting the measurement readings. Furthermore, it is also possible for the central control unit to vary at least one parameter of the measurement arrangement for the optimization of the measurement value logging, depending on the realized positions of the optical scan unit.

Aside from the variation of the pattern generation via the pattern generating unit, the central control unit can, for optimization of the measurement value logging, also vary, e.g., the control parameters of the control unit for the scan unit in dependence of its realized positions.

The central control unit, through one-time or periodic comparison of the realized and the desired positions, analyzes the previously mentioned transfer function of the optical scan unit and utilizes said transfer function for the adjustment of scan patterns for achieving improved scan processes. An example thereto is the option, in dependence of the transfer function, of elevating the peaks of the triangular or sawtooth scan patterns, e.g., in order to minimize the time needed for the scan reversal.

In a further advantageous embodiment, the optimal control parameters are determined by the central control unit through the aforementioned transfer function analysis and transmitted to the control unit in the control circuit of the optical scan unit. For example, optimal parameters can be those which avoid the aforementioned overshoots or "creeping approximation" during the pattern generation.

In a further advantageous embodiment, the interference relations in the two-beam interferometer are varied position-dependently by the central control unit in dependence of the realized positions of the optical scan unit.

In order to ensure great signal strength in all areas of the scan, it is, for example, advantageous in this context to change the polarization adjustment between measurement and reference arm in an OCT interferometer for a scan over a structure with position-dependent double refraction, such as the human cornea. This quick change of the polarization adjustment can be made for example through rotated birefringent wave plates, motor-driven fiber paddles, birefringent or polarization-rotating liquid crystal modulators or quick electro-optical polarization modulators, such as Pockels cells. A further realization of said method is, for example, the position-dependent change of the intensity of the measurement or reference arm in an OCT interferometer, e.g., in order to position-dependently control the sensitivity or the signal-to-noise ratio. This, for example, is possible with known variable optical attenuators.

Furthermore, the optical delay between measurement and reference arm can be varied position-dependently, particularly in dependence of the actually realized positions of the optical scan unit. This can be realized, for example by fast variable optical attenuator units, such as fiber stretchers or the aforementioned RSOD's. For example, said position-dependent delay is particularly advantageous when the scan depth realized by an OCT system is smaller than the axial area in which a curved sample surface extends at extensive lateral scanning, such as a retina or a cornea, allowing for the measurement window to be tracking position-dependently. This is particularly advantageous in combination with TD- and SS-OCT since the quick variation of the optical delay causes no signal loss or fringe washout as would be the case with SD-OCT.

In another embodiment of this variation, the optimal control parameters are determined by the central control unit through the aforementioned transfer function analysis and transmitted to an additional fixation unit, positioned in the measurement arrangement for optimization of the measurement value logging. With this variation, for example, the scan area of the scan unit can be expanded with the aid of eye movements of the patient. This is accomplished through positional change (refixation) of the fixation marker.

Hereby, the use of a control circuit for minimizing the nominal-actual difference is only optional. Instead of a control system, only one control without feedback signal can, in principle, be realized, whereby interferences and deviations are detectable and correctable through the position detection. In this case, damping against interferences is preferably still realized, for example, mechanical damping for quick suppression of the effects of external jolts or vibrations.

Figure 2B:
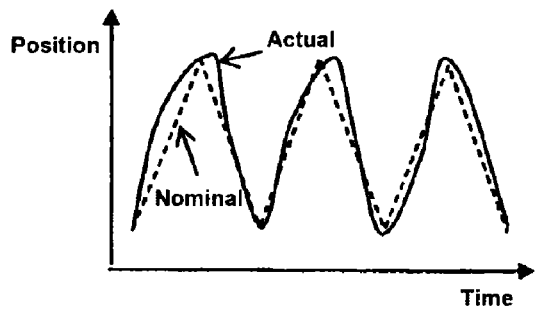

In a graph, FIG. 2*b* depicts a predetermined nominal pattern (dotted line) as well as an actual pattern (solid line).

The utilized term regarding position shall hereby encompass spatial positions and positions of the optical scan unit during pattern generation. As already mentioned, these can be determined in different ways, for example, capacitively, resistively, inductively, or through position or angle specifications of a light beam, deflected by the optical scan unit itself. Hereby, this can also refer to a section of the measurement beam, which, for example is separated from the main part of the measurement beam by a beam splitter, and the current positions of which are detected during the scan pattern generation by at least one spatial resolution sensor.

Thereby, it is particularly advantageous when the position determinations of the optical scan unit take place not only with regard to parts of the biometric system but also with regard to the generally moving eye. As a result, not only deviations and interferences in the scan pattern generation are taken into consideration but, simultaneously, disruptive eye movements as well.

This can take place directly, for example, through camera mapping of the positions of the measurement beam reflections on the cornea, or indirectly, whereby the positional information of the scan unit, with reference to the biometric system, are complemented by the positions of the eye, with reference to the biometric system, which, e.g., are also detectable through camera mapping.

In contrast to the prior art, the position signals in the solution, according to the invention, are used primarily for detecting the actual positions of the measurement beam deflection during pattern generation and not, as in prior art, for the realization of very precise and/or very linear scan patterns. Therefore, the demands on the linearity of the position signals are much lower here, particularly if the nonlinearities can be ascertained through a calibration and corrected during the signal processing for the determination of the biometric values of images, particularly tomograms.

Such a calibration of the position measurement can take place only once or regularly by means of reference structures, e.g., with the help of an external test eye or internal spatial test structures. If direct deflections of the optical scan unit are detected, a position measurement calibration can be effected through moving towards stops or end position sensors, such as fork couplers, etc.

The control circuits shown in the individual embodiments of the invention are primarily meant to suppress and dampen external interferences, such as jolts, vibrations, etc., whereby certain nonlinearities in the feedback signal generation are acceptable.

In another (not depicted) embodiment, the scan unit consists of two galvanometer mirrors. For the detection of the actual positions of the galvanometer mirrors, the closed control circuit exhibits, for example, two one-dimensional position sensors, which are connected to the central control unit. In an alternative embodiment, a two-dimensional spatial resolution sensor can also be used.

In these first two embodiment variations, the current positions of the galvanometer mirrors of the scan unit, according to the invention, are detected relative to the moments of signal detection through A-scans and are used for the determination of biometric data through correction of the measurement data. Furthermore, the detected current positions can be used to correct tomogram distortions.

Figure 2C:
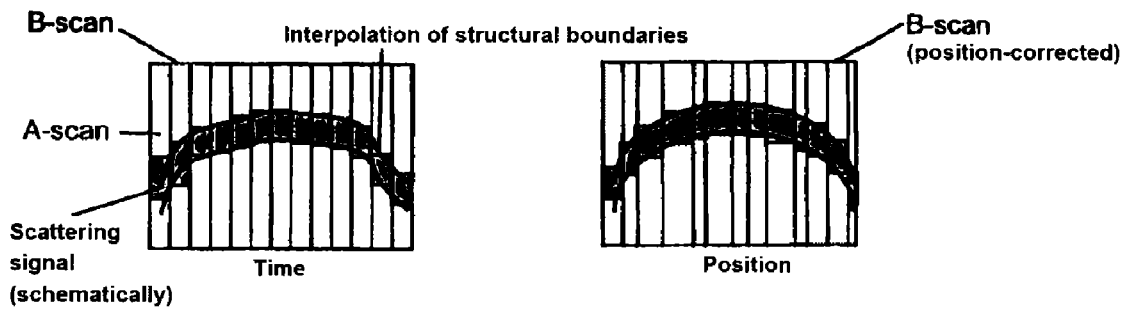

Thereto, FIG. 2*c* shows the juxtaposition of a distorted (left) and a distortion-corrected (right) tomogram, whereby the vertical lines represent the boundaries of the A-scans. The arched curves represent interpolated boundaries of an exemplary structure, e.g., a cornea, the scattering signals of which are depicted schematically in gray. While the left side shows a tomogram, distorted due to hypothetical scan interferences, for which temporally equidistant A-scans were recorded and applied over the timeline, the A-scans for the tomogram on the right side were applied proportionally to their actual positions and therefore spatially corrected.

The interferences shown as examples in the drawing above the timeline could have been caused, e.g., by a scan unit with varying scan speed, which operates unevenly but otherwise could be realized with little effort.

Due to the detection and allowance for the actual scan movement by the position detection, according to the invention, a spatial correction of a tomogram distortion is now possible (FIG. 2c, right), whereby the individual A-scans are applied over the positions, which were realized at the moment of their mapping through the optical scan unit, detected by the position sensor and transmitted to the control unit. Aside from the spatial correction of tomogram distortions, a determination of spatially corrected biometric values, such as curvature parameters of corneas, is hereby also possible.

The allowance for the actual current positions of the galvanometer mirrors, i.e., the utilization for correction of the measurement values is shown in FIG. 2c in such a way that the vertical lines in the right illustration, which represent the temporally equidistant A-scans, no longer exhibit the same distances. However, even here it is possible to complete distorted tomograms in such a way that additional sampling points at non-equidistant points are calculated through mathematical interpolation methods.

Figure 2D:
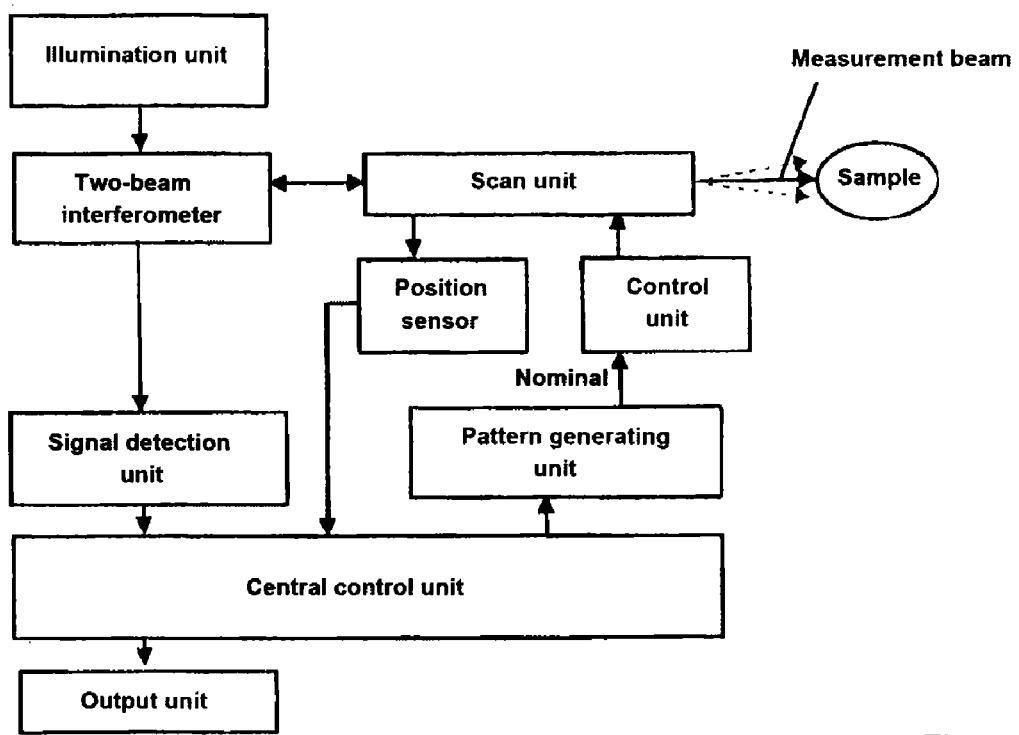
FIG. 2d is a functional schematic of an ophthalmological biometric system, according to an embodiment of the invention, without a control circuit or control loop.

FIG. 2d depicts a version of the biometric system, according to the invention, without a control circuit. This version is simpler than the one shown in FIG. 2a but exhibits greater sensitivity with regard to external mechanical interferences, such as vibrations. However, said sensitivity can in turn be reduced through an increased mechanical or electrical damping at the optical scan unit.

In another embodiment, the position sensor for optimization of the measurement value logging is connected via a trigger unit with the signal detection unit, hence activating the signal detection once a predetermined position of the galvanometer mirror is reached and therefore triggering the measurement value logging.

Figure 3A:
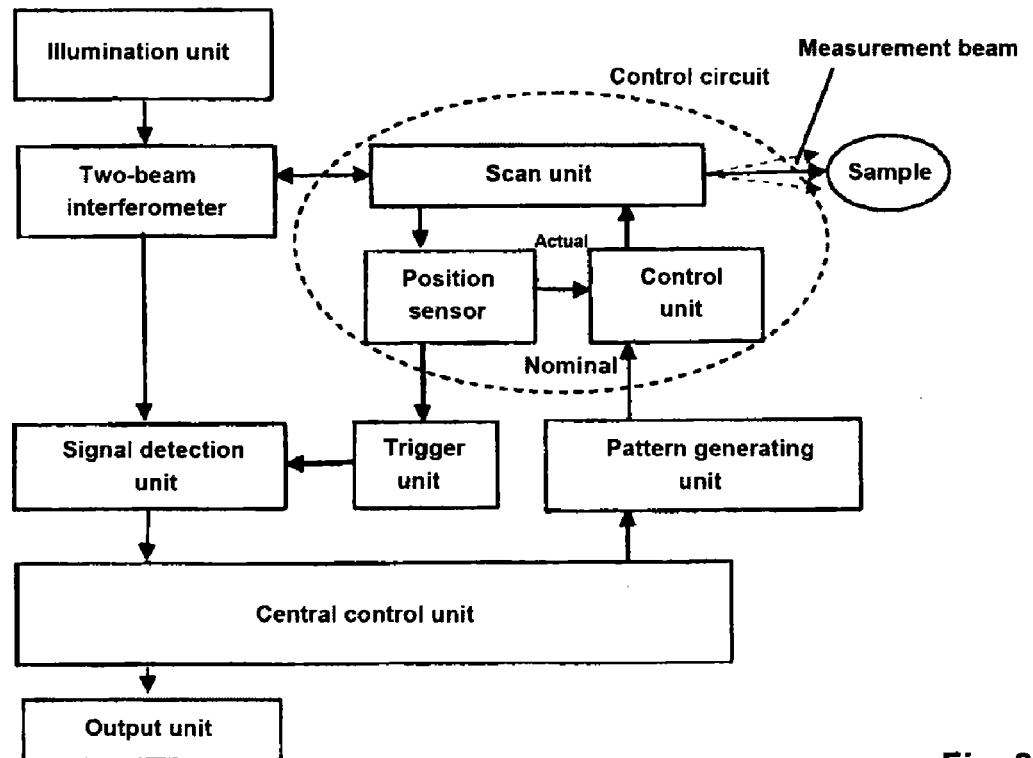
FIG. 3a is a functional schematic of an ophthalmological biometric system, according to an embodiment of the invention, with trigger unit for position-dependent control of the signal detection unit.
Figure 3B:
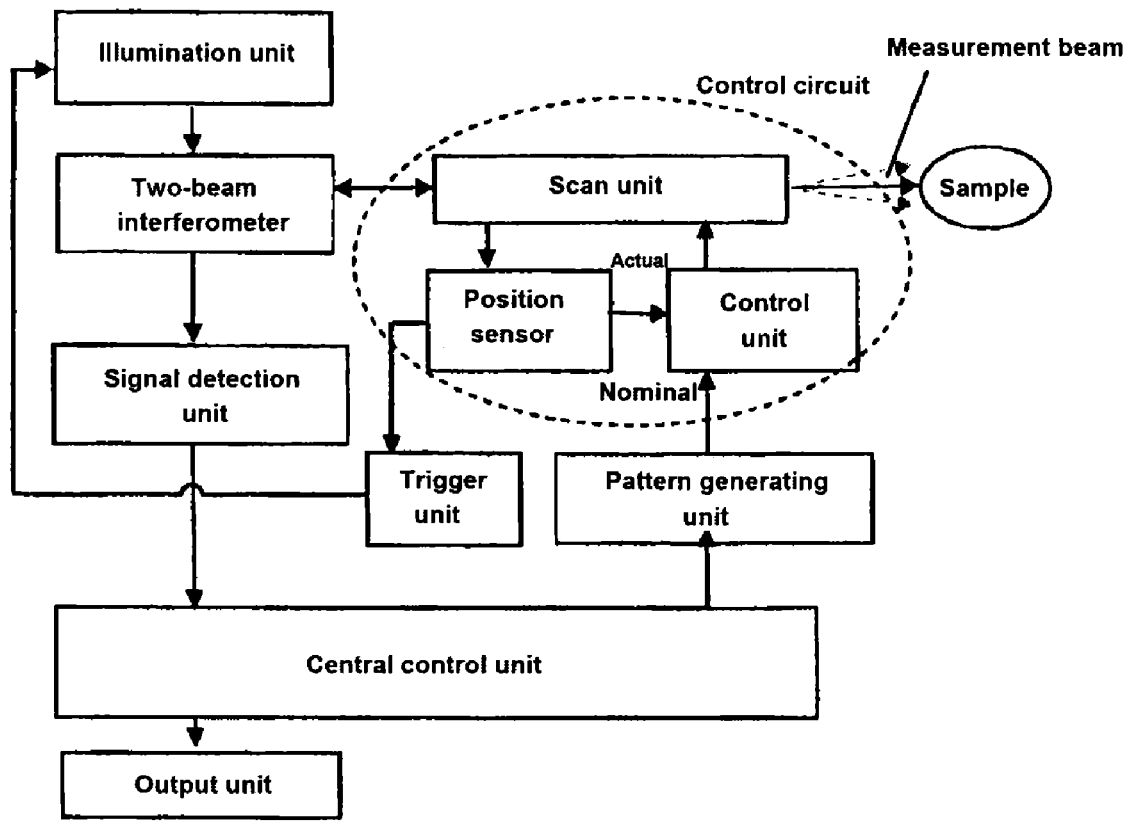
FIG. 3b is a functional schematic of an ophthalmological biometric system, according to an embodiment of the invention, with trigger unit for position-dependent control of the illumination unit.

Thereto, FIG. 3a is a functional schematic of a further scan unit for ophthalmological biometric systems according to an embodiment of the invention. The difference from the embodiment of FIG. 2a can be found in the additional trigger unit which is connected to the signal detection unit.

In this embodiment, signal detection is only activated and measurement value logging triggered once the trigger unit determines that the galvanometer mirror has reached a predetermined position. Therefore, the positional information is, in principle, contained in the scan sequence of the signals and can later be reconstructed through indexing of the scan values and comparison with the positions predetermined for the trigger points. Thereto, it is possible to utilize a trigger value table in order to realize, e.g., certain spatial but inevitably non-equidistant trigger positions for A-scan images and to take them into consideration in the subsequent analysis.

In a further embodiment of said variation, the position sensor for optimization of the measurement value logging is connected with the illumination unit via a trigger unit, therefore activating the illumination unit once a predetermined position of the galvanometer mirror is reached and triggering the measurement value logging.

Figure 3C:
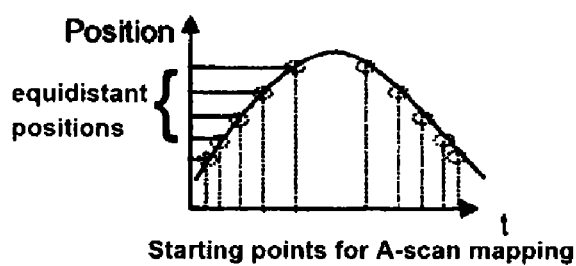

This allows for the direct recording of laterally equidistant measurement data since the A-scans are only triggered once the predetermined positions are reached (at equal distances) and measurements recorded. The results are proper scans which do not require subsequent distortion corrections. This is depicted in the position-time diagram of a triggered scan pattern in FIG. 3c. Once predetermined, herein equidistantly spaced, positions are reached by the measurement beam or the scanner, A-scan mapping is triggered by the trigger unit, e.g., by starting the exposure time of the spectrometer camera in an SD-OCT system.

Analogously, however, the tuning of the source in an SS-OCT is also controllable in order to realize position-dependent images of A-scans. Thereby, A-scans with constant as well as variable scan duration can be realized.

However, in the first scenario it is disadvantageous that not all available photons can be utilized, and in the second scenario it is disadvantageous that varying photon numbers would be registered, which would subsequently lead to different signal-to-noise ratios in the A-scans.

This problem is solved for all OCT versions, particularly SD-OCT's, by connecting the illumination unit scan-position-dependently. For example, the superluminescent diode in a typical SC-OCT system can be activated after individually predetermined imaging positions are reached and deactivated after emission of a predetermined number of photons. Thereby, a constant signal-to-noise ratio is achieved and the photons backscattered from the sample are optimally utilized.

The ophthalmological biometric and image-producing system, according to the invention, is capable of using the realized positions of the optical scan unit, transmitted from the position sensor to the central control unit, in such a way that biometric measurements as well as images, particularly tomograms, can be corrected.

The essential advantages of the invention are found in the small numerical effort for the determination of the biometric data and/or the distortion correction of images as well as in a more efficient scanning of the desired structures of the eyes and/or samples.

In order to increase the accuracy of distortion-corrected images, particularly tomograms, it is hereby possible to calculate additional sampling points at spatially equidistant or non-equidistant points through mathematical interpolation methods.

Thereto, the realized deflections of the optical scan unit, which are measured by the position sensor and transmitted to the central control unit, as well as the measurements of the signal detection unit are used to interpolate position-corrected, biometric measurements or images, particularly tomograms, at positions not measured or even non-measurable.

A frequent, mostly age-related degradation phenomenon of the eye is the cataract which is treated through surgical removal of the eye lens and implantation of an artificial lens (IOL). In order to achieve a desired post-operative refraction of the eye, generally an emmetropic state, careful selection of the artificial lens for the individual eye is required.

The eye length is an essential parameter for the selection process. According to prior art, the optical determination of the eye length is effected by means of the so-called dual-beam short coherence interferometry (DE 198 57 001 A1) or by means of the OCT method (U.S. Pat. No. 7,400,410 B2) through an A-scan along a measuring axis, usually the visual axis, from the vertex of cornea to the fovea.

Since the measuring of the eye length must also be possible through natural eye lenses which are greatly clouded by a cataract, the measuring systems to be used must be highly sensitive. Depending on the design of the measuring system, an interference of the signal detection can occur during measurements directly on the vertex of cornea due to the specular reflection of the measuring light on the tear film of the eye, e.g., through overdriving of the dynamic range of a utilized OCT system. As a result, a direct measurement of the axis length of the eye beginning at the vertex of the cornea can be extremely difficult or even impossible.

In patent application JP 2008-188047 it is suggested to compensate the measurement error, which occurs when the measurement does not take place along the fixation line, by way of calculation. Thereby, the correction is based on a photographic measurement of the misalignment of the measurement beam. However, such a measurement is elaborate and the correction contains errors.

Contrary to this solution from the prior art, the biometric measurements or image data can be corrected, in dependence of the realized positions of the optical scan unit, with the ophthalmological biometric or image-producing system, according to the invention.

In a particularly advantageous embodiment, the transmitted realized deflections of the optical scan unit in connection with the measurements of the signal detection unit are utilized by the central control unit in order to interpolate position-corrected, biometric measurements or image data at positions not measured or non-measurable.

This allows for a particularly advantageous application. After the position of the vertex of the cornea has been determined through interpolation, the axis length of the eye can be determined in simple fashion with great accuracy.

Figure 4:
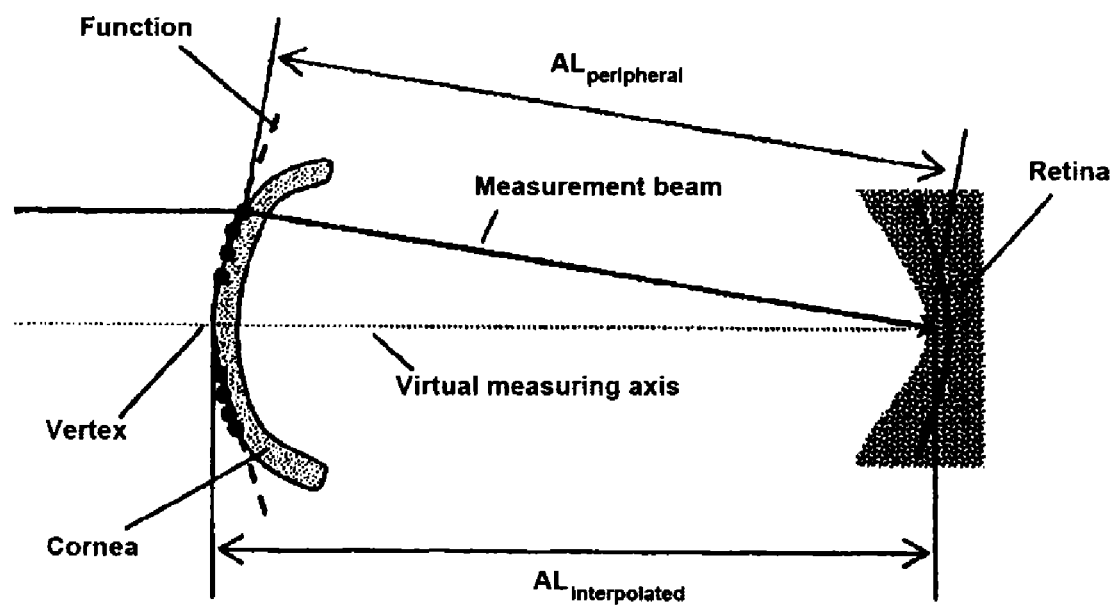
FIG. 4 is a schematic diagram of a B-scan along a path through the vertex of cornea.

According to the schematic diagram in FIG. 4, a B-scan is effected along a path through the vertex of the cornea. Thereto, a B-scan of an OTC measurement beam is effected along a path which runs through the vertex of the cornea, whereby the individual measurements are marked with dots on the cornea. Hereby, the B-scan does not have to comprise A-scans at the location of the vertex of the cornea. However, FIG. 4 shows that the (peripheral) measurement beams would lead to an incorrect determination of the axis length of the eye. Only through interpolation of the surface of the cornea can the exact axis length at the vertex of the cornea be determined along the now virtual measuring axis to the fovea.

The signals in the resulting B-scan image, which correspond to the boundary layers of the cornea and retina, are approximated with suitable continuous and continuously differentiable functions, and the optical eye length is determined from the distance of the functional values in the vertex.

Advantageously, the measurement, which provides a plane section through the eye, is effected with a single B-scan. Said plane section must be effected through the vertex or its immediate proximity. However, in the proximity of the vertex, the specular reflection can lead to an overdriving of the measuring system and render the measurement data in this location useless. In such event, the respective data for the approximation to the fitting function is not taken into account.

While the measurement of the eye length currently takes place along discreet directions, which are manually adjusted by the operator, a sequence of adjacent measurements along a defined path are effected automatically, according to the invention. From said sequence of measurements, the value for the eye length can be determined accurately and in a short amount of time even in difficult situations.

In the method for detection and analysis of measurement data of an ophthalmological biometric and image-producing system, according to the invention, an eye is illuminated with at least one measurement beam from an illumination unit, whereby said beam is deflected by an optical scan unit, and a light portion, scattered or reflected back from the eye, is detected by a signal detection unit and transmitted to a central control unit with output unit for processing, analysis, and storage. Hereby, the scan movement of the scan unit is controlled via a control unit by a central control unit-activated pattern generating unit and its realized deflections are measured by a position sensor, whereby control unit, optical scan unit, and position sensor can form a control circuit or control loop. Thereby, the measurement beam of the interferometric measurement arrangement is deflected by an optical scan unit with a scanner control unit, whereby the optical scan unit consists of at least one galvanometer mirror. During the realization of the scan pattern to be realized, which is transmitted by a pattern generator, the actual positions of the galvanometer mirror are detected, appropriately digitalized and, except within the possible control circuit for the optimization of the measurement value logging, transmitted to a unit of the measurement arrangement or to the central control unit for corrections of the biometric measurements or image data.

In this embodiment of the method, the measurement beam is deflected with only one galvanometer mirror, whereby the deflection can be effected in either one but also two directions. Hereby, the optical scan unit, which consists of only one galvanometer mirror, is positioned in the measurement arm of the two-beam interferometer and includes a closed control circuit for the realization of the scan movements and damping of mechanical interferences. The detection of the actual positions of the galvanometer mirror is hereby effected with the means of a position sensor. Even though the position sensor can be based on different measurement principles, such as capacitive, inductive, potentiometric, magneto-strictive, or the like, optical position sensors are beneficial since the optical position detection is precise and, above all, not susceptible to interference due to triangulation or intensity modulation.

The term "two-beam interferometer" is hereby not limited to the classic two-beam interferometers, such as Michelson or Mach-Zehnder interferometer. Furthermore, variations of Michelson or Mach-Zehnder interferometers as measurement arrangement are conceivable, which exhibit several reference or measurement arms. With such measurement arrangements, according to US 2008/0285043 A1 and DE 10 2007 046 507 A1, for example, several measurement areas can be detected simultaneously.

Hereby, the measurement value logging in the form of B- and C-scans as well as volume scans takes place through applicable deflection of the measurement beam of the interferometric measurement arrangement with the help of a scan unit in the form of a galvanometer mirror. Thereto, the central control unit activates the pattern generation, which transmits a respective scan pattern to the control of the scan unit.

In a closed control circuit, the realization of the scan pattern to be mapped is effected with the help of the scanner control and a position sensor. Thereto, the actual positions of the galvanometer mirror are detected by the position sensor during the realization of the scan pattern and transmitted to the central control unit. With the help of such transmitted, actual positions of the galvanometer mirror, the measurements are appropriately corrected. Furthermore, it is also possible that at least one parameter of the measurement arrangement is varied by the central control unit for optimization of the measurement value logging, in dependence of the realized positions of the optical scan unit.

Aside from the variation of the pattern generation via the pattern generating unit, the central control unit can, for optimization of the measurement value logging, also vary, e.g., the control parameters of the control unit for the scan unit in dependence of its realized positions.

The central control unit, through one-time or periodic comparison of the realized and the desired positions, realizes the previously mentioned transfer function of the optical scan unit and utilizes said transfer function for the adjustment of scan patterns for achieving improved scan processes. An example thereto is the option, in dependence of the transfer function, of elevating the peaks of the triangular or sawtooth scan patterns, e.g., in order to minimize the time needed for the scan reversal.

In a further advantageous embodiment, the optimal control parameters are determined by the central control unit through the aforementioned transfer function and transmitted to the control unit in the control circuit or control loop of the optical scan unit. For example, optimal parameters can be those which avoid the aforementioned overshoots or "creeping approximation" during the pattern generation.

In a further advantageous embodiment, the interference relations in the two-beam interferometer are varied position-dependently by the central control unit in dependence of the realized positions of the optical scan unit.

In order to ensure great signal strength in all areas of the scan, it is advantageous in this context, for example, to change the polarization adjustment between measurement and reference arm in an OCT interferometer for a scan over a structure with position-dependent double refraction, such as the human cornea. This quick change of the polarization adjustment can be effected, e.g., through rotated birefringent wave plates, motor-driven fiber paddles, birefringent or polarization-rotating liquid crystal modulators or quick electro-optical polarization modulators, such as Pockels cells. A further realization of said method is, for example, the position-dependent change of the intensity of measurement or reference arm in an OCT interferometer, e.g., in order to position-dependently control the sensitivity or the signal-to-noise ratio. This, for example, is possible with known variable optical attenuators.

Furthermore, the optical delay between measurement and reference arm can be varied position-dependently, particularly in dependence of the actually realized positions of the optical scan unit. This can be realized, e.g., by means of fast variable optical attenuator units, such as fiber stretchers or the aforementioned RSODs. For example, said position-dependent delay is particularly advantageous when the scan depth realized by an OCT system is smaller than the axial area in which a curved sample surface extends at extensive lateral scanning, such as a retina or a cornea, allowing for the measurement window to be tracking position-dependently.

This is particularly advantageous in combination with TD- and SS-OCT since the quick variation of the optical delay causes no signal loss or fringe washout as would be the case with SD-OCT.

In another embodiment of this variation, the optimal control parameters are determined by the central control unit through aforementioned transfer function analysis and transmitted to an additional, in the measurement arrangement positioned, fixation unit for optimization of the measurement value logging. With this variation, for example, the scan area of the scan unit can be expanded with the aid of eye movements of the patient. This is accomplished through positional change (refixation) of the fixation marker.

Hereby, the use of a control circuit for minimizing the nominal-actual difference is only optional. Instead of a control system, only one control without feedback signal can, in principle, be realized, whereby interferences and deviations are detectable and correctable through the position detection. In this case, damping against interferences is preferably still realized, for example, mechanical damping for quick suppression of the effects of external jolts or vibrations.

In these two embodiment of the method, the current positions of the galvanometer mirrors of the scan unit, according to the invention, are detected relative to the moments of signal detection through A-scans and used for the determination of biometric data through correction of the measurement data or for correcting image distortions, particularly tomogram distortions.

According to the methods of prior art, tomograms are recorded in such a way that, preferably in time and space, equidistant A-scans are realized and documented accordingly in proportion to time. Even though the realization of the scan pattern to be mapped is controlled by a nominal-actual comparison, positional deviations can lead to distortions of the recorded tomogram during the scan process.

As a result, spatially undisturbed tomograms, according to prior art, can be achieved only as approximation and with great effort and demands on the optical scan unit and its control.

In a method, according to the invention, the current positions realized by the optical scan unit are detected with regard to the moments of the signal detection of the A-scans and utilized for later corrections of the measurement data. As a result, tomograms can, e.g., be distortion-corrected, whereby the measurements are depicted via a position coordinate while considering the actually realized positions. For example, a tomogram can be depicted exactly with regard to the capacitively detected rotation angle of a deflecting galvanometer mirror or also with regard to the position of an OCT measurement beam in several dimensions relative to the sample, the time-dependent path data of which is registered during the mapping of a volume scan by means of optical sensors with spatial resolution and transmitted together with the OCT data to the central control unit, stored and used for the correction of the OCT data.

In another embodiment of the method, the position sensor transmits the position data for optimization of the measurement value logging to a trigger unit, which controls the signal detection unit position-dependently. In this variation of the method, signal detection is only activated and measurement value logging triggered, once the trigger unit determines that the galvanometer mirror has reached a predetermined position. The positional information are in principle contained in the scan sequence of the signals and can later be reconstructed through indexing of the scan values and comparison with the positions predetermined for the trigger points. It is possible to utilize a trigger value table thereto in order to realize, e.g., certain spatial but inevitably non-equidistant trigger positions for A-scan images and to take them into consideration in the subsequent analysis.

In a further embodiment of said method variation, the position sensor transmits the position data for optimization of the measurement value logging to a trigger unit which is connected to an illumination unit, therefore activating the illumination unit once a predetermined position of the galvanometer mirror is reached and triggering the measurement value logging.

The position-dependently controlled illumination unit also allows for the direct recording of laterally equidistant measurement data since the A-scans are only triggered once the predetermined positions are reached (at equal distances) and measurements recorded. The results are proper scans which do not require subsequent distortion corrections. Once predetermined, herein equidistantly spaced, positions are reached by the measurement beam or the scanner, A-scan mapping is triggered by the trigger unit, e.g., by starting the exposure time of the spectrometer camera in an SD-OCT system.

Analogously, however, the tuning of the source in an SS-OCT is controllable in order to realize position-dependent images of A-scans. Thereby, A-scans with constant as well as variable scan durations can be realized. However, in the first scenario it is disadvantageous that not all available photons can be utilized, and in the second scenario it is disadvantageous that varying photon numbers would be registered, which would subsequently lead to different signal-to-noise ratios in the A-scans.

This problem is solved for all OCT versions, particularly SD-OCT, by connecting the illumination unit scan-position-dependently. For example, the superluminescent diode in a typical SC-OCT system can be activated after individually predetermined imaging positions are reached and deactivated after emission of a predetermined number of photons. Thereby, a constant signal-to-noise ratio is achieved and the photons backscattered from the sample are optimally utilized.

In order to increase the accuracy of distortion-corrected tomograms, it is hereby possible to calculate additional sampling points at spatially equidistant or non-equidistant points through mathematical interpolation methods.

Hereby, the use of a control circuit for minimizing the nominal-actual difference is only optional. Instead of a control system, only one control without feedback signal can, in principle, be realized, whereby interferences and deviations are detectable and correctable through the position detection. In this case, damping against interferences is preferably still realized, for example, mechanical damping for quick suppression of the effects of external jolts or vibrations.

Thereby, the realized deflections of the optical scan unit, which are measured by the position sensor and transmitted to the central control unit, as well as the measurements of the signal detection unit are used to interpolate position-corrected, biometric measurements or tomograms at positions not measured or even non-measurable.

A frequent, mostly age-related degradation phenomenon of the eye is the cataract which is treated through surgical removal of the eye lens and implantation of an artificial lens (IOL). In order to achieve a desired post-operative refraction of the eye, generally an emmetropic state, careful selection of the artificial lens for the individual eye is required.

The eye length is an essential parameter for the selection process. According to prior art, the determination of the eye length is effected by means of the so-called dual-beam short coherence interferometry (DE 198 57 001 A1) or by means of the OCT method (U.S. Pat. No. 7,400,410 B2) through an A-scan along a measuring axis, usually the visual axis from the vertex of cornea to the fovea.

Since the measuring of the eye length must also be possible through natural eyes which are greatly clouded by a cataract, the measuring systems to be used must be highly sensitive. Depending on the design of the measuring system, an interference of the signal detection can occur during measurements directly on the vertex of cornea due to the specular reflection of the measuring light on the tear film of the eye, e.g., through overdriving of the dynamic range of a utilized OCT system. As a result, a direct measurement of the axis length of the eye at the vertex of cornea can be extremely difficult or even impossible.

In patent application JP 2008-188047 it is suggested to compensate the measurement error, which occurs when the measurement does not take place along the fixation line, by way of calculation. Thereby, the correction is based on a photographic measurement of the misalignment of the measurement beam. However, such a measurement is elaborate and the correction contains errors.

In contrast, the axis length of an eye can be determined with the method for measurement value logging in an ophthalmological biometric or image-producing system, according to the invention, in a robust and very accurate fashion through the position-corrected detection of biometric data and images, particularly tomograms.

In this embodiment of the method, according to the invention, a B-Scan is effected along a path through the vertex of the cornea. Thereto, a B-scan of an OTC measurement beam is effected along a path which runs through the vertex of the cornea, whereby the individual measurements are marked with dots on the cornea. Hereby, the B-scan does not have to comprise A-scans at the location of the vertex of the cornea.

Thereby, it has to be taken into consideration that the (peripheral) measurement beams would lead to an incorrect determination of the axis length of the eye. Only through interpolation of the surface of the cornea can the exact axis length at the vertex of the cornea be determined along the now virtual measuring axis to the fovea.

The signals in the resulting B-scan image, which correspond to the boundary layers of the cornea and retina, are approximated with suitable continuous and continuously differentiable functions, and the optical eye length is determined from the distance of the functional values in the vertex.

Advantageously, the measurement, which provides a plane section through the eye, is effected with a single B-scan. Said plane section must be effected through the vertex or its immediate proximity. However, in the proximity of the vertex, the specular reflection can lead to an overdriving of the measuring system and render the measurement data in this location useless. In such event, the respective data for the approximation to the fitting function are not taken into account.

While the measurement of the eye length currently takes place along discreet directions, which are manually adjusted by the operator, a sequence of adjacent measurements along a defined path are effected automatically in accordance with the invention. From said sequence of measurements, the value for the eye length can be determined accurately and in a short amount of time even in difficult situations.

The described method is not only useful for axis length measurements but can, in principle, be applied to other sectional measurements on the eye, for example, measurements of the internal or external anterior chamber depth or the thickness of the crystal lens since in these cases interfering specular reflections can appear directly on the desired measuring axes.

In a further advantageous embodiment of the method, the actual positions of the galvanometer mirror, which are detected by every position sensor and transmitted to the central control unit, are additionally utilized for triggering the measurement value logging, whereby the signal detection is activated and therefore triggered only when a predetermined position of the galvanometer mirror is reached.

As in the previously described embodiments of the method, the measurement value logging in the form of B- and C-scans as well as volume scans is effected through applicable deflection of the measurement beam of the interferometric measurement arrangement with the help of a scan unit, whereby the central control unit activates the pattern generation, which transmits a respective pattern to the control of the scan unit.

Once again, with the help of the scanner control and a position sensor, a possibly interference insensitive, control-based realization of the scan pattern to be depicted is effected in a closed control circuit. In addition, the positions, actually realized by the optical scan unit, are detected by the position sensor during the generation of the scan pattern and transmitted to the central control unit.

Contrary to the previously described method variations, the actual positions of the galvanometer mirror are additionally utilized for triggering the measurement value logging. Now, the signal detection is activated and therefore triggered only when a predetermined position of the galvanometer mirror is reached This allows for the direct recording of laterally equidistant measurement data since the A-scans are only triggered once the predetermined positions are reached (at equal distances) and measurements recorded. The results are proper scans which do not require subsequent distortion corrections.

The essential advantages of this embodiment variation are found in the small numerical effort for the determination of the biometric data and/or the distortion correction of images, particularly tomograms, as well as in a more efficient scanning of the desired structures of the eyes.

The ophthalmological biometric system and the method for measurement value logging, according to the invention, provides a solution, whereby the known disadvantages from prior art are remedied and which is significantly more cost-effective and less elaborate. In addition, it allows for mapping of undistorted tomograms.

This was mainly achieved in such a way that significantly fewer demands with regard to reproducibility and accuracy for the realization of a predetermined deflection pattern are put on the suggested cost-effective deflection system and no great demands are put on the linearity of the realized scan. The control electronics utilized hereby primarily serve the damping of external interferences, and are, therefore, also simple and cost-effective.

The suggested solution can find use in biometric systems, which are based on time-domain OCT (TD-OCT) as well as frequency-domain OCT (FD-OCT). In the time-domain method for the determination of the measurements, the reference arm is adjusted in length and the intensity of the interference measured continuously, allowing, for example, for a signal-optimizing tracking of the focusing of the measurement beam during imaging of individual A- or C-scans (U.S. Pat. No. 5,847,827 A). In comparison, the method known as frequency-domain or also Fourier-domain OCT allows for very quick and efficient detection of complete A-scans through parallel detection of spectral interferences and reconstruction by means of the Fourier transformation.

The frequency-domain method can, in dependence of the utilized illumination unit, be subdivided into simultaneous and sequential methods. The simultaneous method, which requires a broadband illumination unit, is also called (parallel) spectral-domain method (SD-OCT). In comparison, an adjustable illumination unit (U.S. Pat. No. 7,414,779 B2) with variable wavelength is used in the simultaneous method, whereby the sequential frequency-domain method is also called swept-source method (SS-OCT). Biometric systems which operate along the lines of both methods are also possible.

In the following, advantages of this very simple and cost-efficient ophthalmological biometric or image-producing system can be seen:

Pattern generation with a certain error acceptance (noise, quantization leaps, etc.) as well as little demand on the reproducibility of the patterns;

Utilization of nonlinear scans, e.g., sinusoidal scans (significant reduction of the mechanical demands on the scan unit);

Control circuits for the deflection unit are not required and/or require significantly fewer technical efforts;

Demands regarding temperature stability are significantly lower;

Acceptance regarding external influences, such as interferences or vibrations, microphonics effects, etc. is significantly greater and would, in an extreme case, even correct disturbed spatial sequences of the recorded A-scans;

Determination of biometric measurements, such as eye length, lens thickness, anterior chamber depth, etc. with a single B-scan;

and larger and heavier mirrors can be utilized.

The aforementioned units (pattern generating unit, signal detection unit, trigger unit, control unit, etc.) can, in principle, also be modules of functional units of the central control unit without exceeding the protective scope of the claimed invention.

The invention claimed is:

1. An ophthalmological biometric or image-producing system, comprising: a measurement arrangement with an illumination unit that illuminates the eye with at least one measurement beam; a signal detection unit that captures light scattered or reflected back from the eye; a central control unit including an output unit and a central control unit-activated pattern generating unit which includes an optical scan unit, a control unit that controls the optical scan unit's deflection of at least one measurement beam with regard to the eye structures; a position sensor that measures realized deflections of the optical scan unit; wherein the control unit, the optical scan unit, and the position sensor either form a control loop or do not form a control loop; wherein the position sensor, in addition to connection within the control loop if the control loop is present, comprises a connection to a unit of the measurement arrangement that optimizes measurement value logging or a connection to the central control unit that corrects the biometric measurements or image data.

2. The ophthalmological biometric or image-producing system, according to claim 1, wherein the signal detection unit that detects the light scattered back from the eye comprises a two-beam interferometer including a measurement arm and wherein the scan unit is positioned in the measurement arm.

3. The ophthalmological biometric or image-producing system, according to claim 1, wherein the position sensor that optimizes the measurement value logging comprises connections to the central control unit, which, varies at least one parameter of the measurement arrangement dependent upon the realized positions of the optical scan unit.

4. The ophthalmological biometric or image-producing system, according to claim 1 wherein the position sensor that optimizes the measurement value logging comprises connections to the central control unit, which varies the pattern generation of the pattern generating unit dependent upon the realized positions of the optical scan unit.

5. The ophthalmological biometric or image-producing system, according to claim 1, wherein the position sensor that optimizes the measurement value logging comprises connections to the central control unit, which varies the control parameters of the control unit dependent upon the realized positions of the optical scan unit.

6. The ophthalmological biometric or image-producing system, according to claim 1, wherein the position sensor that optimizes the measurement value logging comprises a connection to the central control unit, which varies the interference relations in the two-beam interferometer position-dependently dependent upon the realized positions of the optical scan unit.

7. The ophthalmological biometric or image-producing system, according to claim 1, wherein the position sensor that optimizes the measurement value logging is connected to a fixation unit, additionally positioned in the measurement arrangement.

8. The ophthalmological biometric or image-producing system, according to claim 1, wherein the position sensor that optimizes the measurement value logging is connected to the signal detection unit via a trigger unit.

9. The ophthalmological biometric or image-producing system, according to claim 1, wherein the position sensor that optimizes the measurement value logging is connected to the illumination unit via a trigger unit.

10. The ophthalmological biometric or image-producing system, according to claim 1, wherein the position sensor that corrects the biometric measurements or image data comprises connections to the central control unit, which corrects the biometric measurements or image data position-dependently dependent upon the realized positions of the optical scan unit.

11. The ophthalmological biometric or image-producing system, according to claim 1, wherein the position sensor for the correction of the biometric measurements or image data comprises connections to the central control unit which utilizes the transmitted realized deflections of the optical scan unit in connection with the measurements of the signal detection unit to interpolate position-corrected, biometric measurements or image data at positions that are not measured or that are non-measurable.

12. The ophthalmological biometric or image-producing system, according to claim 9, wherein the position sensor for the correction of the biometric measurements or image data comprises connections to the central control unit which utilizes the transmitted realized deflections of the optical scan unit in connection with the measurements of the signal detection unit to interpolate position-corrected, biometric measurements or image data at positions that are not measured or that are non-measurable.

13. Ophthalmological biometric or image-producing system, according to claim 1, wherein the position sensor for the correction of the biometric measurements or image data comprises connections to the central control unit which utilizes the transmitted realized deflections of the optical scan unit in connection with the measurements of the signal detection unit to interpolate the position of a vertex of cornea and determine an axis length of the eye therefrom.

14. Ophthalmological biometric or image-producing system, according to claim 10, wherein the position sensor for the correction of the biometric measurements or image data comprises connections to the central control unit which utilizes the transmitted realized deflections of the optical scan unit in connection with the measurements of the signal detection unit to interpolate the position of a vertex of cornea and determine an axis length of the eye therefrom.

15. Ophthalmological biometric or image-producing system, according to claim 11, wherein the position sensor for the correction of the biometric measurements or image data comprises connections to the central control unit which utilizes the transmitted realized deflections of the optical scan unit in connection with the measurements of the signal detection unit to interpolate the position of a vertex of cornea and determine an axis length of the eye therefrom.

16. A computer implemented method of detection and analysis of measurement data of an ophthalmological biometric and image-producing system, comprising illuminating an eye with at least one measurement beam from an illumination unit in a measurement arrangement, the measurement beam being deflected by an optical scan unit; detecting light scattered or reflected back from the eye by a signal detection unit and transmitting the scattered or reflected back light to a central control unit with an output unit for processing, analysis, and storage; controlling the scan unit via a control unit by a central control unit-activated pattern generating unit; and measuring realized deflections by a position sensor, wherein the control unit, optical scan unit, and position sensor either form a control loop or do not form a control loop; wherein the position sensor measures the realized positions of the optical scan unit and, in addition to transmission within the control loop if the control loop is present, transmits said positions to a unit of the measurement arrangement for the optimization of the measurement value logging or to the central control unit for corrections of the biometric measurements or image data.

17. The method for detection and analysis of measurement data, according to claim 16, wherein the scan unit is positioned in a measurement arm of a two beam interferometer and further comprising detecting the light scattered back from the eye via the two-beam interferometer.

18. The method for detection and analysis of measurement data, according to claims 16, wherein the position sensor transmits the positional data for the optimization of the measurement value logging to the central control unit, which, dependent on the realized positions of the optical scan unit, varies at least one parameter of the measurement arrangement.

19. The method for detection and analysis of measurement data, according to claim 16, wherein the position sensor transmits the positional data for the optimization of the measurement value logging to the central control unit, which varies the pattern generation of the pattern generating unit dependent upon the realized positions of the optical scan unit.

20. The method for detection and analysis of measurement data, according to claim 16, wherein the position sensor transmits the positional data for the optimization of the measurement value logging to the central control unit, which varies the control parameters of the control unit dependent upon the realized positions of the optical scan unit.

21. The method for detection and analysis of measurement data, according to claim 16, wherein the position sensor transmits the positional data for the optimization of the measurement value logging to the central control unit, which varies the interference relations in the two-beam interferometer position-dependently dependent upon the realized positions of the optical scan unit.

22. The method for detection and analysis of measurement data, according to claim 16, wherein the position sensor transmits the positional data for the optimization of the measurement value logging to a fixation unit, additionally positioned in the measurement arrangement, which controls a fixation marker through positional change.

23. The method for detection and analysis of measurement data, according to claim 16, wherein the position sensor transmits the positional data for the optimization of the measurement value logging to a trigger unit, which position-dependently controls the signal detection unit.

24. The method for detection and analysis of measurement data, according to claim 16, wherein the position sensor transmits the positional data for the optimization of the measurement value logging to a trigger unit, which position-dependently controls the illumination unit.

25. The method for detection and analysis of measurement data, according to claim 16, wherein the position sensor transmits the positional data for the correction of the biometric measurements or image date to the central control unit.

26. The method for detection and analysis of measurement data, according to claim 16, wherein the realized deflections of the optical scan unit, measured by the position sensor and transmitted to the central control unit, are utilized in connection with the measurements of the signal detection unit in order to interpolate position-corrected, biometric measurements or image data at positions not measured or non-measurable.

27. The method for detection and analysis of measurement data, according to claim 16, wherein the central control unit interpolates the position of the vertex of the cornea from the transmitted measurements of the position sensor and the signal detection unit and determines the axis length of the eye therefrom.

28. The method for detection and analysis of measurement data, according to claim 26, wherein the central control unit interpolates the position of the vertex of the cornea from the transmitted measurements of the position sensor and the signal detection unit and determines the axis length of the eye therefrom.

* * * * *

UNITED STATES PATENT AND TRADEMARK OFFICE
CERTIFICATE OF CORRECTION

| | | |
|---|---|---|
| PATENT NO. | : 8,388,135 B2 | Page 1 of 1 |
| APPLICATION NO. | : 12/886155 | |
| DATED | : March 5, 2013 | |
| INVENTOR(S) | : Martin Hacker et al. | |

It is certified that error appears in the above-identified patent and that said Letters Patent is hereby corrected as shown below:

In the Specification

Col. 10, line 57, after "of" insert --the--

Col. 15, line 36, after "of" insert --the--

Col. 15, line 42, after "of" insert --the--

Col. 15, line 46, after the second occurrence of "of" insert --the--

In the Claims

Col. 19, line 32, after the second occurrence of "of" insert --the--

Col. 19, line 40, after the second occurrence of "of" insert --the--

Col. 19, line 48, after the second occurrence of "of" insert --the--

Col. 20, line 10, delete "claims" and insert --claim--

Col. 20, line 56, delete "date" and insert --data--

Signed and Sealed this
Nineteenth Day of August, 2014

Michelle K. Lee
*Deputy Director of the United States Patent and Trademark Office*